United States Patent [19]

Weber

[11] Patent Number: 5,780,718
[45] Date of Patent: Jul. 14, 1998

[54] MOISTURE SENSOR

[75] Inventor: Klaus Weber, Kronberg, Germany

[73] Assignee: VDO Adolf Schindling AG, Frankfurt, Germany

[21] Appl. No.: 650,095

[22] Filed: May 17, 1996

[30] Foreign Application Priority Data

Jul. 8, 1995 [DE] Germany ............... 195 24 943.7

[51] Int. Cl.$^6$ .............. H01G 5/20; G08B 21/00; B60S 1/08; G01R 27/26
[52] U.S. Cl. ............. 73/29.01; 73/335.05; 324/664; 324/71.1; 324/694; 29/610.1; 29/851; 29/832; 340/602
[58] Field of Search ............. 73/29.01, 335.05; 324/664, 694, 71.1; 29/610.1, 611, 620, 851, 860, 832; 340/602, 604

[56] References Cited

U.S. PATENT DOCUMENTS

| | | | |
|---|---|---|---|
| 2,993,815 | 7/1961 | Treptow | 117/212 |
| 3,647,532 | 3/1972 | Friedman et al. | 117/212 |
| 3,748,625 | 7/1973 | Bennewitz | 338/34 |
| 3,906,426 | 9/1975 | Frazee et al. | 338/35 |
| 3,983,527 | 9/1976 | Ohsato et al. | 338/35 |
| 4,050,048 | 9/1977 | Frazee | 338/35 |
| 4,072,771 | 2/1978 | Grier, Sr. | 427/96 |
| 4,163,384 | 8/1979 | Blakemore | 73/29 |
| 4,172,922 | 10/1979 | Merz et al. | 428/432 |
| 4,326,404 | 4/1982 | Mehta | 73/29 |
| 4,540,604 | 9/1985 | Siuta | 427/96 |
| 4,554,493 | 11/1985 | Armstrong | 318/444 |
| 4,639,831 | 1/1987 | Iyoda | 361/286 |
| 4,642,887 | 2/1987 | Fredriksson | 29/611 |
| 4,644,139 | 2/1987 | Harrison et al. | 219/522 |
| 4,737,629 | 4/1988 | Iwama et al. | 250/231 R |
| 4,805,070 | 2/1989 | Koontz et al. | 361/286 |
| 4,815,198 | 3/1989 | Ramus | 29/611 |
| 4,827,198 | 5/1989 | Mueller | 318/483 |
| 4,831,493 | 5/1989 | Wilson et al. | 316/286 |
| 4,870,746 | 10/1989 | Klaser | 29/620 |
| 4,919,744 | 4/1990 | Newman | 156/308 |
| 5,039,840 | 8/1991 | Boardman | 219/270 |
| 5,040,411 | 8/1991 | Medzius | 73/73 |
| 5,048,336 | 9/1991 | Sugihara et al. | 73/336.5 |
| 5,054,190 | 10/1991 | Inoue et al. | 29/611 |
| 5,319,975 | 6/1994 | Pederson et al. | 73/335.01 |
| 5,323,637 | 6/1994 | Bendicks et al. | 73/29.01 |
| 5,467,522 | 11/1995 | Gold | 29/611 |
| 5,598,146 | 1/1997 | Schröder | 340/602 |

*Primary Examiner*—Hezron E. Williams
*Assistant Examiner*—J. David Wiggins
*Attorney, Agent, or Firm*—Martin A. Farber

[57] ABSTRACT

A rain sensor for the windshield of a vehicle has one or more electrically conductive layers which are arranged in a given pattern upon the outer surface of such windshield, and is constructed as a laminate of conductive and resistive layers formed by process steps of printing and sintering for construction of electrodes of the sensor. A conductive layer is formed of a mixture of electrically conductive particles and a glass frit which melts at a lower temperature than a melting temperature of the material of the window which serves as a support for the sensor. The conductive paste is applied with a heating action step, in the configuration of an electrode structure, by sintering to the window.

26 Claims, 2 Drawing Sheets

MOISTURE SENSOR

FIELD AND BACKGROUND OF THE INVENTION

The present invention relates to the construction of a sensor for detecting moisture on a non-conductive support, in particular the windshield of a motor vehicle, having one or more electrically conductive layers which are arranged in a given pattern upon the outer surface of the support.

Electrically conductive layers on car windows serve, for example, to form a resistive rain sensor. However, they can also be used for the electric heating of the window or to form an antenna for a radio. Such conductive paths should adhere as firmly as possible to the window so that they cannot loosen from it upon the cleaning of the window, or as a result of environmental influences. This applies, in particular, to conductive paths which serve as rain sensor since such rain sensors must lie within the wiping field of the windshield wiper and the windshield wiper moves constantly over the conductive paths upon the wiping of the window. Aside from adhering firmly to the window of the car, such conductive paths should, for this reason, also be as abrasion resistant as possible. Furthermore, the maintaining of precise dimensions of the conductive paths is frequently necessary.

In order to satisfy these requirements, conductive paths are now being applied by vapor deposition onto car windows. Vapor deposition methods are, however, very expensive and result in undesirably large deviations in dimension so that sufficiently reproducible sensor signals cannot be obtained with a sensor which is formed of such conductive paths.

SUMMARY OF THE INVENTION

It is an object of the present invention to provide a sensor of the aforementioned type which both adheres well to the support and has a high resistance to mechanical abrasion.

According to the invention, the conductive layer is a sintered layer produced by printing techniques using a conductive paste, the conductive paste containing conductive particles and a glass frit which melts at a lower temperature than the material of the support. By this development, as a result of the sintering, the sensor is imparted a high degree of adherence to the support, while the molten glass frit forms a smooth abrasion-resistant surface.

An exact structure of the pattern of the electrically conductive layer is obtained by producing the conductive layer by a screen-printing technique. The conductive layer is preferably a resistance layer.

If the conductive particles are platinum particles, then not only the molten glass frit but also the conductive particles have a high resistance to abrasion.

If the conductive paste contains a support liquid which evaporates at a temperature substantially below the melting point of the glass frit, then only the glass frit and the conductive particles remain on the support after the sintering.

The sensor can have a pattern with at least two path-shaped conductive layers (1, 1') extending a slight distance apart from each other, the path-shaped conductive layers (1, 1') which extend alongside of each other being adapted to being connected to different electric potentials.

If the ends of the path-shaped conductive layers (1, 1') are conducted around a side edge (4) of the support onto the inner surface of the support then, without expensive wiring, the connector of the sensor can be connected to a source of electric power inside the motor vehicle.

The sensor is preferably a resistive rain sensor having resistance between two path-shaped conductive layers (1, 1'). The resistance is dependent on the amount of moisture covering both of the two layers.

The support may consist of various materials. It is particularly favorable, in particular also with respect to the abrasion behavior in the case of windows which are moved over by windshield wipers, for the support to be a glass window.

If, between the support and the resistance layer, a conductive path of high electric conductivity is arranged on the support, then the resistance value to be detected depends substantially only on the amount of moisture covering the sensor and less on the specific conductivity thereof.

A sensor in accordance with the invention is produced in simple fashion in the manner that the conductive paste is applied in the desired pattern by a screen printing process onto the outer surface of the pane of glass and sintered onto the pane of glass by the action of heat.

In another method for the production of the sensor, the conductive paste can be applied in a desired pattern onto a flexible foil (5) and dried, the flexible foil (5) can be applied to the outer surface of the glass window, and the glass window together with the foil (5) can be subjected to heat in order to burn away the foil (5) and effect the sintering of the conductive paste onto the pane of glass. This makes it possible not only to produce the sensor pattern independently of the pane of glass, which is generally bulky, and then apply it to the latter, but, in addition, also permits a simple application to curved windows due to the flexibility of the foil.

These advantages are obtained also in another method of producing the sensor in which the conductive paste is applied in the desired pattern onto a support sheet (8) and dried. A side of the support sheet (8) bearing the conductive paste is covered with a flexible foil layer (9). Adherence of the foil layer to the conductive-paste pattern is greater than an adherence of the support sheet (8) to the conductive-paste pattern. The support sheet (8) is separated from the foil layer (9) bearing the conductive-paste pattern, and the foil layer (9) is applied on the outer surface of the pane of glass. The pane of glass together with the foil layer (9) is acted on by heat to burn away the foil layer (9) and sinter the conductive paste on the pane of glass.

The foil (5) or the foil layer (9) is preferably a plastic film which evaporates without residue upon the sintering.

The sintering can be effected at a temperature which corresponds approximately to the deformation temperature for the plastic deformation of the pane of glass, the sintering being effected at a temperature of between about 500° C. and 700° C., and preferably at a temperature of about 600° C.

If the conductive paste is applied to the flat pane of glass and sintered on it with simultaneous deformation by bending of the pane of glass, then the sintering-on and the shaping of the pane of glass take place in a single operation.

The bending can in this connection take place both by gravity bending and by press bending in a press-bending furnace.

In order furthermore to be able, by means of the separately prepared sensor pattern, to prepare the conductive path of high electric conductivity separately from the pane of glass, a conductive path of high electric conductivity can be applied onto the conductive paste after the application and possible drying of the conductive paste on the flexible foil (5). Alternatively, the conductive paste can be applied on a conductive path of higher electrical conductivity which is applied in a desired pattern onto the support sheet.

A sensor arrangement suitable for the foregoing process can be developed, in one embodiment of the invention, by applying the desired pattern consisting of a sinterable conductive paste on a flexible foil (5). Then the flexible foil (5) is evaporated at a temperature corresponding approximately to the sintering temperature of the conductive paste.

In another embodiment, the desired pattern of a sinterable conductive paste is arranged on a support sheet (8), and a flexible foil layer (9) is applied on the support sheet (8) over the conductive paste pattern. Adherence of the conductive paste pattern to the support sheet (8) is less than its adherence to the foil layer (9). The flexible foil layer (9) evaporates at a temperature corresponding approximately to the sintering temperature of the conductive paste.

Both embodiments permit simple application of the sensor onto the pane of glass.

BRIEF DESCRIPTION OF THE DRAWINGS

With the above and other objects and advantages in view, the present invention will become more clearly understood in connection with the detailed description of preferred embodiments when considered with the accompanying drawings, of which.

DETAILED DESCRIPTION OF THE PREFERRED EMBODIMENTS

Figure 1:
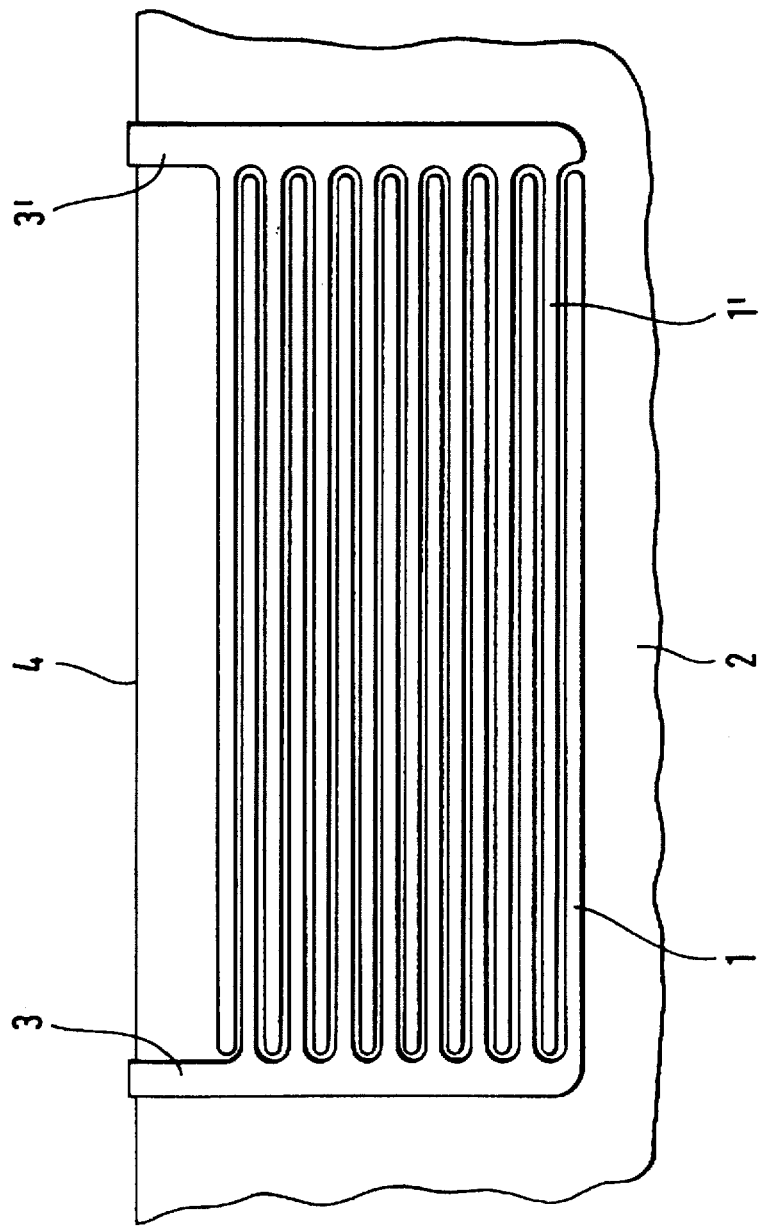
FIG. 1 is a top view of a sensor.

The rain sensor shown in FIG. 1 consists of two electrically conductive resistance layers 1 and 1' applied to the outer surface of a windshield 2, the layers being developed in comb-like manner and having the teeth of their combs engaging into each other so that only slots of a slight width are present between the teeth. Each resistance layer 1 and 1' has a connection contact 3 and 3', respectively, which is conducted around the side edge 4 of the windshield 2 onto the inner surface of the windshield 2, and can be connected to a respective terminal of electrical potential. By conductive bridging of the slots by drops of water impinging on the windshield 2, a conductive connection is produced between the teeth, the detectable resistance of which depends on the number of water drops bridging over the slots.

The teeth of the resistant layers 1 and 1' can have a width on the order of magnitude of 100 μm, and the slots between the teeth can have a width on the order of magnitude of 400 μm.

Figure 2:
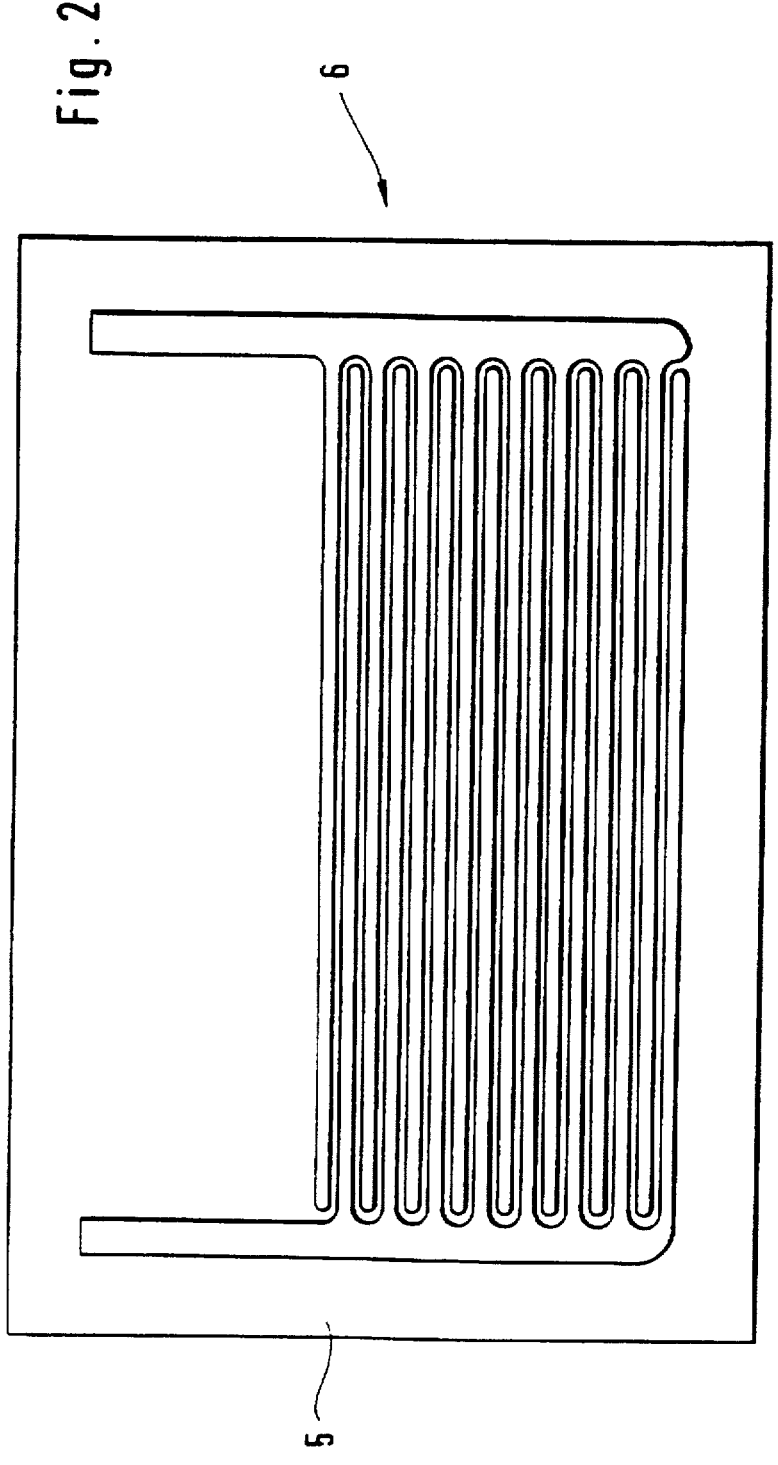
FIG. 2 is a top view of a sensor arrangement.
Figure 3:
FIG. 3 is a side view of the sensor arrangement of FIG. 2.
Figure 4:
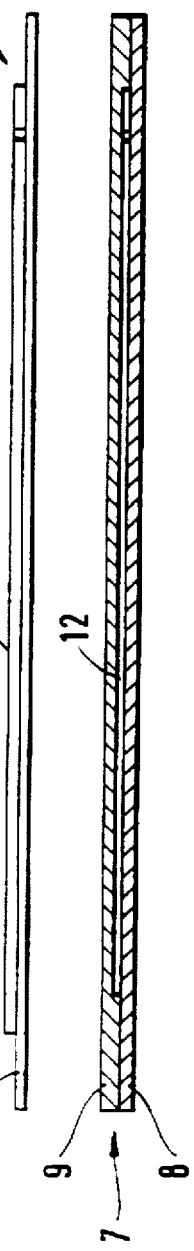
FIG. 4 is a cross section through another embodiment of a sensor arrangement.

In FIGS. 2 to 4, sensor arrangements 6 and 7 are shown of two alternately applied preferred embodiments which are produced separately from the windshield 2 and then applied to the windshield 2. In the embodiment of the sensor arrangement 6 shown in FIGS. 2 and 3, a conductive paste 12 which contains platinum particles and glass frit is applied onto a flexible foil or layer 5 of a synthetic resin by a screen printing technique in the pattern of the resistance layers 1 and 1', and dried in a drying oven.

This prefabricated foil 5 can now be so placed on a preferably flat windshield 2 such that its connection contacts 5 extend beyond the side edge 4 of the windshield 2 and are folded around it towards the rear of the windshield 2.

Since the foil 5 is of an adhering character, it remains in the position in which it has been applied to the windshield 2. By the action of heat of a temperature of about 600° C. on the windshield 2 in a bending furnace (not shown), there takes place simultaneously a sintering of the conductive paste 12 onto the windshield 2, a gasification or evaporation without residue of the flexible foil 5, and a bending of the windshield 2 out of its flat shape into a curved shape. Upon the application of the foil to the windshield, this can be effected either on the side bearing the conductive paste 12 or on the side of the foil 5 away from the conductive paste 12.

In the embodiment of the sinter arrangement 7 shown in FIG. 4, a conductive paste 12 containing platinum particles and glass frit is applied on a support sheet 8 of, for instance, paper, in the pattern of the resistance layers 1 and 1' and dried. Thereupon the surface of the conductive-paste pattern is covered by a plastic paste which, upon drying, forms a flexible foil 9.

If the sensor arrangement 7 has been previously produced in this manner, the support sheet 8 can now be removed in the manner of a decal (decalcomania), and the flexible foil layer 9 can be applied onto the windshield 2 in the same way as the application of the foil 5 in the embodiment of FIGS. 2 and 3, and sintered thereon.

Since the adherence of the conductive paste 12 to the support sheet 8 is substantially less than its adherence to the flexible foil layer 9, the conductive-paste pattern remains on the foil layer 9 upon the separation of support sheet 8 and flexible foil layer 9.

Due to the support sheet 8, the sensor arrangement 7 can be handled in a very practical manner, since there is no danger of an unintended sticking of the flexible foil layer 9 before a pulling off of the support sheet 8 that must precede the sintering of the foil sheet 9.

I claim:

1. A sensor for detecting moisture on a non-conductive support, in particular the windshield of motor vehicle, the sensor comprising one or more electrically conductive layers which are arranged in a given pattern upon the outer surface of the support;

wherein an individual one of the conductive layers is a printed sintered layer of conductive particles and a glass frit which melts at a temperature lower than a melting temperature of a material of the support.

2. A method of constructing a sensor for detecting moisture on a non-conductive support, in particular the windshield of motor vehicle, the sensor comprising one or more electrically conductive layers which are arranged in a given pattern upon the outer surface of the support, the method comprising steps of:

producing a conductive paste of conductive particles and a glass frit which melts at a lower temperature than a melting temperature of a material of the support;

printing said conductive paste on said support in the configuration of said one or more electrically conductive layers; and sintering said conductive paste on to said support by application of heat to produce the conductive layer pattern, a temperature of said sintering being lower than a melting temperature of the support material.

3. A method of constructing a sensor according to claim 2, wherein said printing is accomplished by a screen-printing technique.

4. A sensor for detecting moisture on a non-conductive support, in particular the windshield of motor vehicle, the sensor comprising one or more electrically conductive layers which are arranged in a given pattern upon the outer surface of the support;

wherein an individual one of the conductive layers is a printed sintered layer of conductive particles and a glass frit which melts at a lower temperature than a melting temperature of a material of the support; and a layer of said one or more conductive layers is a chemically modified layer having significantly higher electrical resistance than any other of said one or more conductive layers.

5. A sensor according to claim 1, wherein the conductive particles are platinum particles.

6. A method of constructing a sensor according to claim 2, wherein said conductive paste contains a support liquid; and said sintering includes an evaporating of the liquid at a temperature substantially below the melting point of the glass frit.

7. A sensor according to claim 1, wherein said pattern has at least two path-shaped conductive layers extending a slight distance apart from each other, for connection with terminals of differing electric potentials.

8. A sensor for detecting moisture on a non-conductive support, in particular the windshield of motor vehicle, the sensor comprising one or more electrically conductive layers which are arranged in a given pattern upon the outer surface of the support;

wherein an individual one of the conductive layers is a printed sintered layer of conductive particles and a glass frit which melts at a lower temperature than a melting temperature of a material of the support;

said pattern has at least two path-shaped conductive layers extending a slight distance apart from each other, for connection with terminals of differing electric potentials; and ends of the path-shaped conductive layers form leads that extend around a side edge of the support onto an inner surface of the support.

9. A sensor according to claim 7, wherein the sensor is a resistive rain sensor, the electrical resistance between said two path-shaped conductive layers being dependent on an amount of moisture covering both of the two path-shaped conductive layers.

10. A sensor according to claim 1, wherein the support is a glass window.

11. A sensor for detecting moisture on a non-conductive support, in particular the windshield of motor vehicle, the sensor comprising one or more electrically conductive layers which are arranged in a given pattern upon the outer surface of the support;

wherein an individual one of the conductive layers is a printed sintered layer of conductive particles and a glass frit which melts at a lower temperature than a melting temperature of a material of the support;

said pattern has at least two path-shaped conductive layers extending a slight distance apart from each other, for connection with terminals of differing electric potentials;

the sensor is a resistive rain sensor, the resistance between said two path-shaped conductive layers being dependent on an amount of moisture covering both of the two path-shaped conductive layers;

each of said path-shaped conductive layers is a resistance layer, the sensor further comprising:

a conductive path of high electrical conductivity which is arranged on the support between the support and the resistance layer.

12. A method of constructing a sensor according to claim 3, wherein the conductive paste is applied in said pattern by said screen printing process onto an outer surface of said support and sintered onto said support by the action of heat, said support being a pane of glass.

13. A method of constructing a sensor for detecting moisture on a non-conductive support, in particular the windshield of motor vehicle, the sensor comprising one or more electrically conductive layers which are arranged in a given pattern upon the outer surface of the support, the method comprising steps of:

producing a conductive paste of conductive particles and a glass frit which melts at a lower temperature than a melting temperature of a material of the support;

printing said conductive paste on said support in the configuration of said one or more electrically conductive layers;

sintering said conductive paste onto said support by application of heat to produce the conductive layer pattern; and wherein said support is a glass window, and said step of printing includes steps of:

placing the conductive paste in said pattern on a flexible foil;

drying the paste;

applying the flexible foil to the outer surface of the glass window; and wherein said sintering step includes a step of heating the glass window together with the foil to burn away the foil and effect the sintering of the conductive paste onto the glass window.

14. A method of constructing a sensor for detecting moisture on a non-conductive pane of glass, in particular the windshield of a motor vehicle, the sensor comprising one or more electrically conductive layers which are arranged in a given pattern upon the outer surface of the pane of glass, the method comprising steps of:

producing a conductive paste;

applying said conductive paste on a side of a support sheet in said pattern, and drying said paste;

covering the paste and the side of the support sheet bearing the conductive paste with a flexible foil layer wherein an adherence of the foil layer to the conductive-paste pattern is greater than an adherence of the support sheet to the conductive-paste pattern;

separating said support sheet from said foil layer and said conductive-paste pattern, the later adhering to and being borne by said foil layer;

applying said foil layer with said paste pattern on an outer surface of the pane of glass with said paste contacting the pane of glass; and heating said foil layer and said paste together with said pane of glass to accomplish a burning away of said foil layer and a sintering of the conductive paste on the pane of glass.

15. A method of constructing a sensor according to claim 14, wherein the foil layer comprises a plastic film.

16. A method of constructing a sensor according to claim 15, wherein said sintering is effected at a temperature which corresponds approximately to a deformation temperature for a plastic deformation of the pane of glass.

17. A method of constructing a sensor according to claim 16, wherein the sintering is effected at a temperature of between about 500° C. and 700° C.

18. A method of constructing a sensor according to claim 17, wherein the sintering is effected at a temperature of about 600° C.

19. A method of constructing a sensor according to claim 16, wherein said pane of glass is flat; and said applying and said sintering steps are effective to apply the conductive paste to the flat pane of glass and to sinter the paste on the pane of glass with simultaneous deformation of the glass pane by a bending of the pane of glass.

20. A method of constructing a sensor according to claim 19, wherein bending takes place by gravity bending.

21. A method of constructing a sensor according to claim 19, wherein the bending takes place by press bending in a press-bending furnace.

22. A method of constructing a sensor according to claim 13, further comprising a step, subsequent to said drying step, of:

locating a conductive path of high electric conductivity onto the conductive paste.

23. A method of constructing a sensor according to claim 13, further comprising a step prior to said printing step, of:

providing a conductive path of higher electrical conductivity which is applied in a desired pattern onto the support sheet; and applying the conductive paste on the conductive path of higher electrical conductivity.

24. A method of constructing a sensor for detecting moisture on a non-conductive support, in particular the windshield of a motor vehicle, the sensor comprising one or more electrically conductive layers which are arranged in a given pattern upon the outer surface of the support, the method comprising steps of:

producing a conductive paste;

applying the conductive paste on a flexible foil;

sintering the paste in said pattern of conductive paste on said flexible foil; and evaporating said flexible foil at a temperature corresponding approximately to a sintering temperature of the conductive paste.

25. A method of constructing a sensor for detecting moisture on a non-conductive support, in particular the windshield of a motor vehicle, the sensor comprising one or more electrically conductive layers which are arranged in a given pattern upon the outer surface of the support, the method comprising steps of:

producing a sinterable conductive paste;

locating the paste on a support sheet in said pattern;

applying a flexible foil layer on the support sheet over the conductive paste pattern, an adherence of the conductive paste pattern to the support sheet being less than an adherence of the paste pattern to said foil layer; and evaporating said flexible foil layer at a temperature corresponding approximately to a sintering temperature of the conductive paste.

26. A sensor according to claim 1, wherein the support comprises a glass, the glass frit having a melting temperature lower than a melting temperature of the support glass.

* * * * *